US 6,568,614 B2

(12) United States Patent
Chen et al.

(10) Patent No.: US 6,568,614 B2
(45) Date of Patent: May 27, 2003

(54) RECYCLING APPARATUS BY CRUSHING AND PASTEURIZING USED HYPODERMIC SYRINGES AND COMPRESSING WASTE

(76) Inventors: Han Jong Chen, No. 16, Lane 533, Dajyh Rd., Dali City, Taichung County (TW); Wei Fu Chen, No. 16, Lane 533, Dajyh Rd., Dali City, Taichung County (TW)

( * ) Notice: Subject to any disclaimer, the term of this patent is extended or adjusted under 35 U.S.C. 154(b) by 0 days.

(21) Appl. No.: 09/875,406

(22) Filed: Jun. 5, 2001

(65) Prior Publication Data

US 2002/0179756 A1 Dec. 5, 2002

(51) Int. Cl.⁷ .............................................. B02C 19/12
(52) U.S. Cl. .................... 241/100; 241/101.2; 241/141; 241/606
(58) Field of Search ....................... 241/99, 100, 101.2, 241/141, 606, 101.78, DIG. 38, 236

(56) References Cited

U.S. PATENT DOCUMENTS

| | | | | |
|---|---|---|---|---|
| 3,750,966 A | * | 8/1973 | Anderson | 241/100 |
| 4,628,169 A | * | 12/1986 | Ch'ing-Lung | 241/99 |
| 4,971,261 A | * | 11/1990 | Solomons | 241/100 |
| 5,025,994 A | * | 6/1991 | Maitlen et al. | 241/100 |
| 5,166,488 A | * | 11/1992 | Peppard | 241/606 |
| 5,662,281 A | * | 9/1997 | Wollert et al. | 241/100 |
| 5,887,807 A | * | 3/1999 | Beinecke | 241/100 |
| 6,311,909 B1 | * | 11/2001 | Lin | 241/101.4 |

* cited by examiner

Primary Examiner—John M. Husar
(74) Attorney, Agent, or Firm—Pro-Techtor International Services

(57) ABSTRACT

A recycling apparatus comprises a body; a slit on top having a hole on one end; a rear internal pasteurizing mechanism comprising a pulverizing device and a bottom first container; a front internal crushing mechanism comprising two sets of parallel blade wheels and a bottom second container; and a waste storage mechanism comprising a third container, a spring-loaded lever, and a plunger sliding in the third container. In use sequentially insert the needles of the used syringes into the slit with the piston syringe portion of the syringe held on the slit, push the syringes forward to cause the needles to contact the pulverizing device to be ground into powder while being pasteurized, the powder are dropped into the first container, the remained piston syringe portion of each syringe eventually drops into the crushing mechanism through the hole, the dropped piston syringe portion of each syringe is pressed and cut into pieces by the sets of the blade wheels, and the pieces are dropped into the second container. In another use lift the lever up to allow waste to store in the third container, and push down the lever to cause the plunger to compress the waste.

3 Claims, 5 Drawing Sheets

RECYCLING APPARATUS BY CRUSHING AND PASTEURIZING USED HYPODERMIC SYRINGES AND COMPRESSING WASTE

FIELD OF THE INVENTION

The present invention relates to waste proposal and more particularly to a recycling apparatus for crushing and pasteurizing used hypodermic syringes and compressing waste generated in hospital.

BACKGROUND OF THE INVENTION

A conventional used hypodermic syringe processing apparatus discloses a cutting means including several blades for cutting the hollow metal needle of a used hypodermic syringe into two pieces. However, the previous apparatus suffered from several disadvantages. For example, a used syringe is only cut not crushed. Hence, virus still exists in the cut syringe. In a worse case a person involved in the processing of such syringes may be infected by virus accidentally. Also, part of metal needle is still attached to the piston syringe, thus increasing the difficulty of processing. In other words, it is preferred that needle is separated from piston syringe after cut for ease of subsequent recycling process. Thus improvement exists.

SUMMARY OF THE INVENTION

It is therefore an object of the present invention to provide a recycling apparatus comprising a body; a slit on top of the body having a width only permitting a piston syringe portion of a hypodermic syringe to pass through while holding a hollow metal needle of the syringe thereon, the slit having a hole on one end for permitting the piston syringe portion of the syringe to drop into the body; a rear pasteurizing mechanism inside the body under the slit comprising a pulverizing device for pulverizing the needle of the syringe into powder, a first drive source for driving the pulverizing device, a channel extended downward from the first drive source for guiding the dropped powder, and a bottom first container; a front crushing mechanism inside the body under the hole comprising two sets of parallel blade wheels, a second drive source, a reduction gear for reducing a rotating speed of the second drive source, a loop member coupled between the reduction gear and one set of the blade wheels for transmitting a power of the second drive source to one set of the blade wheels, and a bottom second container, and a waste storage mechanism attached to the front side of the body and comprising a third container, a top downwardly tapered opening, a hinge on the top edge of the third container opposite to the opening, a spring-loaded lever having one end coupled to the hinge, a connecting rod having one end pivotably coupled to the bottom of the lever, and a plunger pivotably coupled to the other end of the connecting rod being capable of sliding in the third container, wherein in one state of use sequentially insert the needles of the used syringes into the slit with the piston syringe portion of the syringe held on the slit, push the used syringes forward to cause the needles of the syringes to contact the pulverizing device to be ground into powder while being pasteurized, the powder are dropped into the first container through the channel, the remained piston syringe portion of each of the syringes eventually drops into the crushing mechanism through the hole, the dropped piston syringe portion of each of the syringes is pressed and cut into pieces by the sets of the blade wheels, and the pieces are dropped into the second container; and in the other state of use lift the lever up to allow waste to store in the third container through the opening, and push down the lever to cause the plunger to compress the waste.

The above and other objects, features and advantages of the present invention will become apparent from the following detailed description taken with the accompanying drawings.

DETAILED DESCRIPTION OF THE PREFERRED EMBODIMENTS

Figure 1:
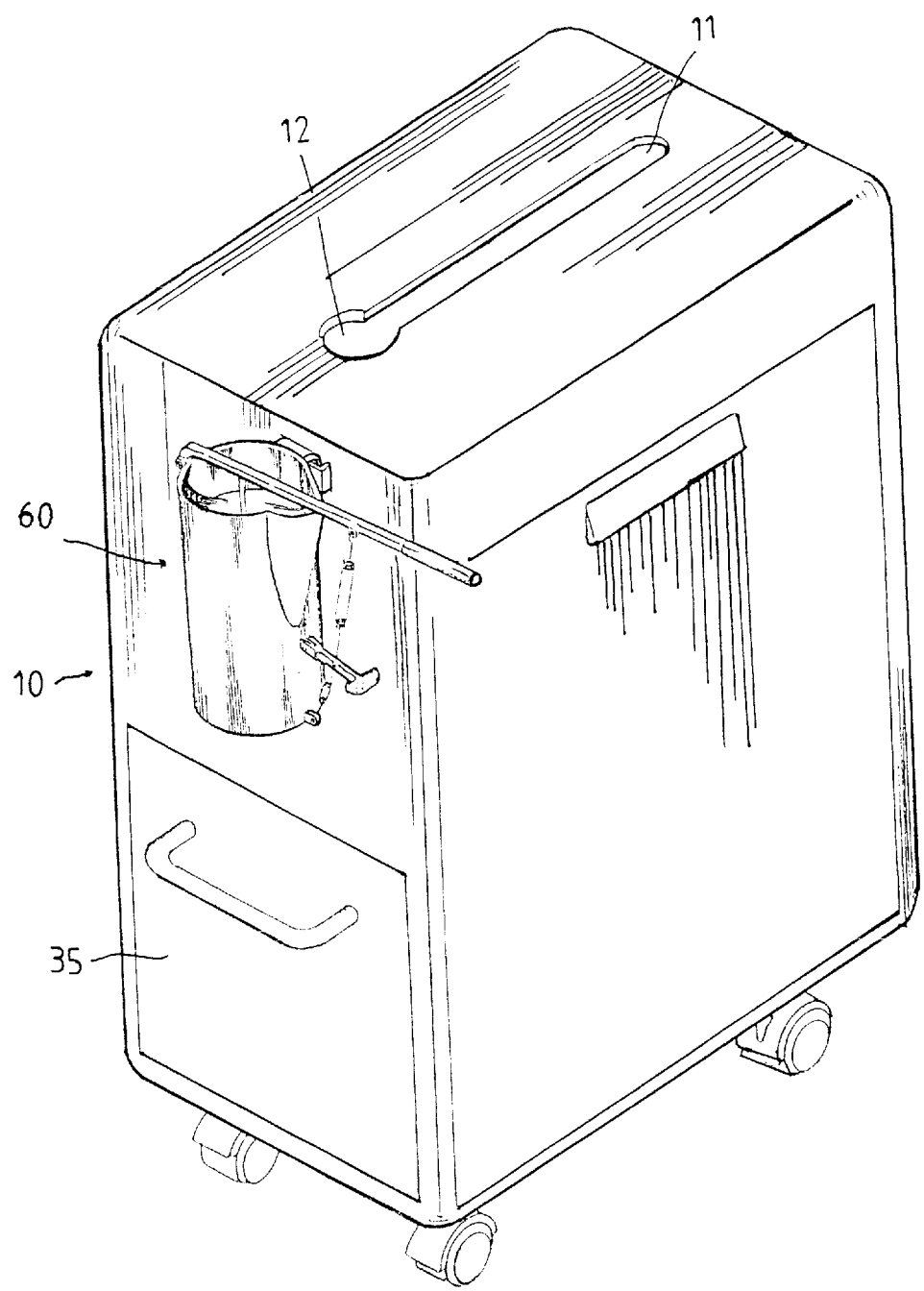
FIG. 1 is a perspective view of a recycling apparatus for crushing and pasteurizing used hypodermic syringes and compressing hospital waste according to the invention.
Figure 2:
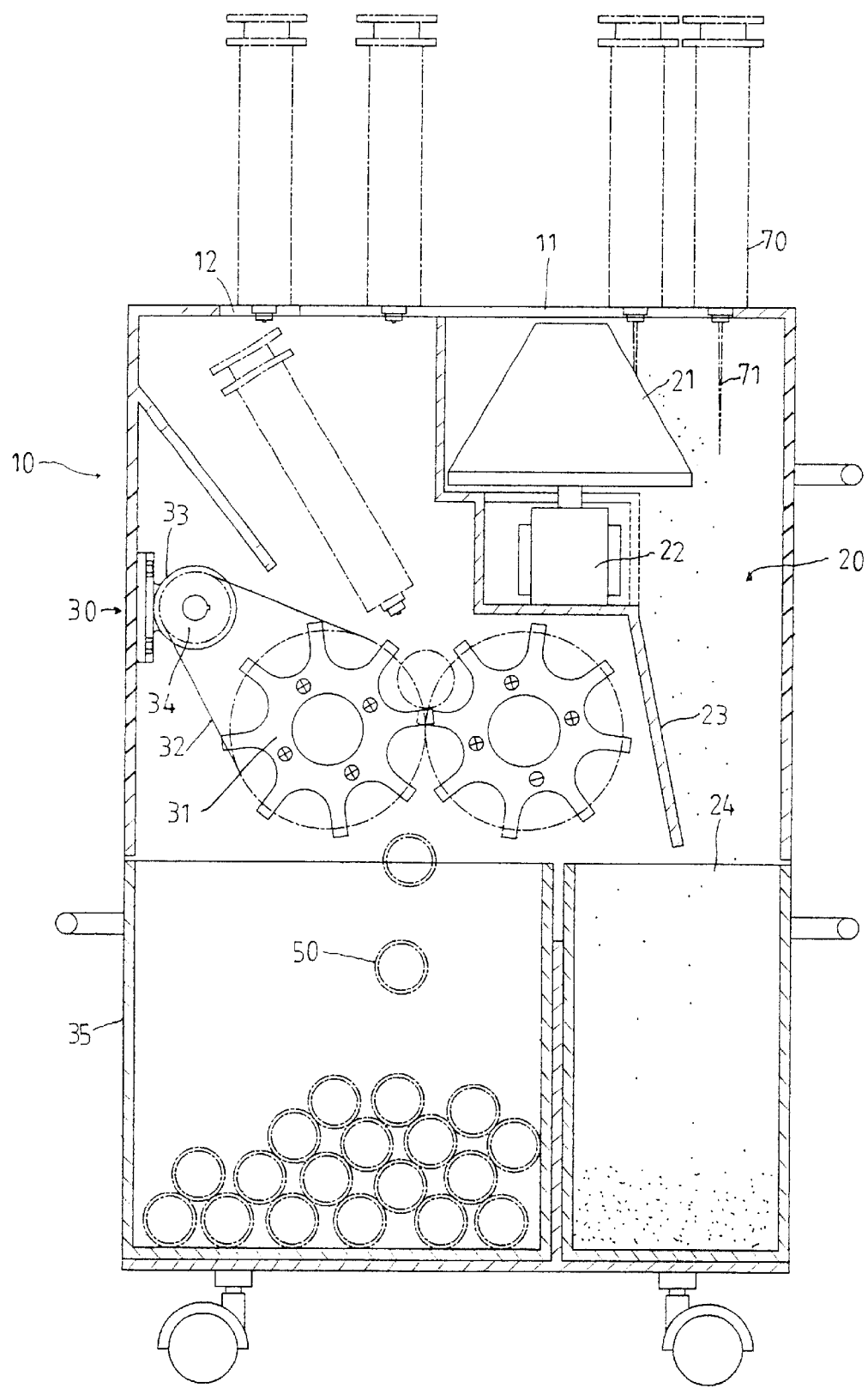
FIG. 2 is a perspective view of FIG. 1 with used syringes disposed on top for processing.

Referring to FIGS. 1 and 2, there is shown a recycling apparatus for crushing and pasteurizing used hypodermic syringes and compressing waste in accordance with the invention comprising a wheeled body 10, a slit 11 on top of body 10 the width thereof only permitting the hollow metal needle of a hypodermic syringe 70 to pass through while holding the piston syringe portion of the hypodermic syringe 70 thereon, a hole 12 formed on one end of slit 11 for permitting the piston syringe portion of hypodermic syringe 70 to drop into the body 10, a rear pasteurizing device 20 inside body 10 under slit 11, a front crushing device 30 inside body 10 under hole 12, and a waste storage device 60 attached to the front side of body 10.

Pasteurizing device 20 comprises a pulverizing device (e.g., grinding wheel) 21 for pulverizing the needle of the hypodermic syringe 70, a first drive source (e.g., motor) 22 under the pulverizing device 21 for driving the pulverizing device 21, a channel 23 extended downward from first drive source 22 for guiding the dropped powder, and a first container 24 under the channel 23 for temporarily storing the powder. Crushing device 30 comprises two sets of coaxial blade wheels 31 with one blade wheel 31 of one set alternating with one blade wheel 31 of the other set, a second drive source (e.g., motor) 33 mounted on the inner front wall of body 10, a reduction gear 34 rotatably coupled to one end of second drive source 33 for reducing the rotating speed of second drive source 33 to a prescribed one, a loop belt 33 coupled between the reduction gear 34 and one set of blade wheels 31 (i.e., left one of FIG. 2 as the drive one) for transmitting the power of second drive source 33 to the coupled set of blade wheels 31, and a second container 35 under the sets of blade wheels 31 for temporarily storing the crushed piston syringe portions of syringes 70.

Figure 3:
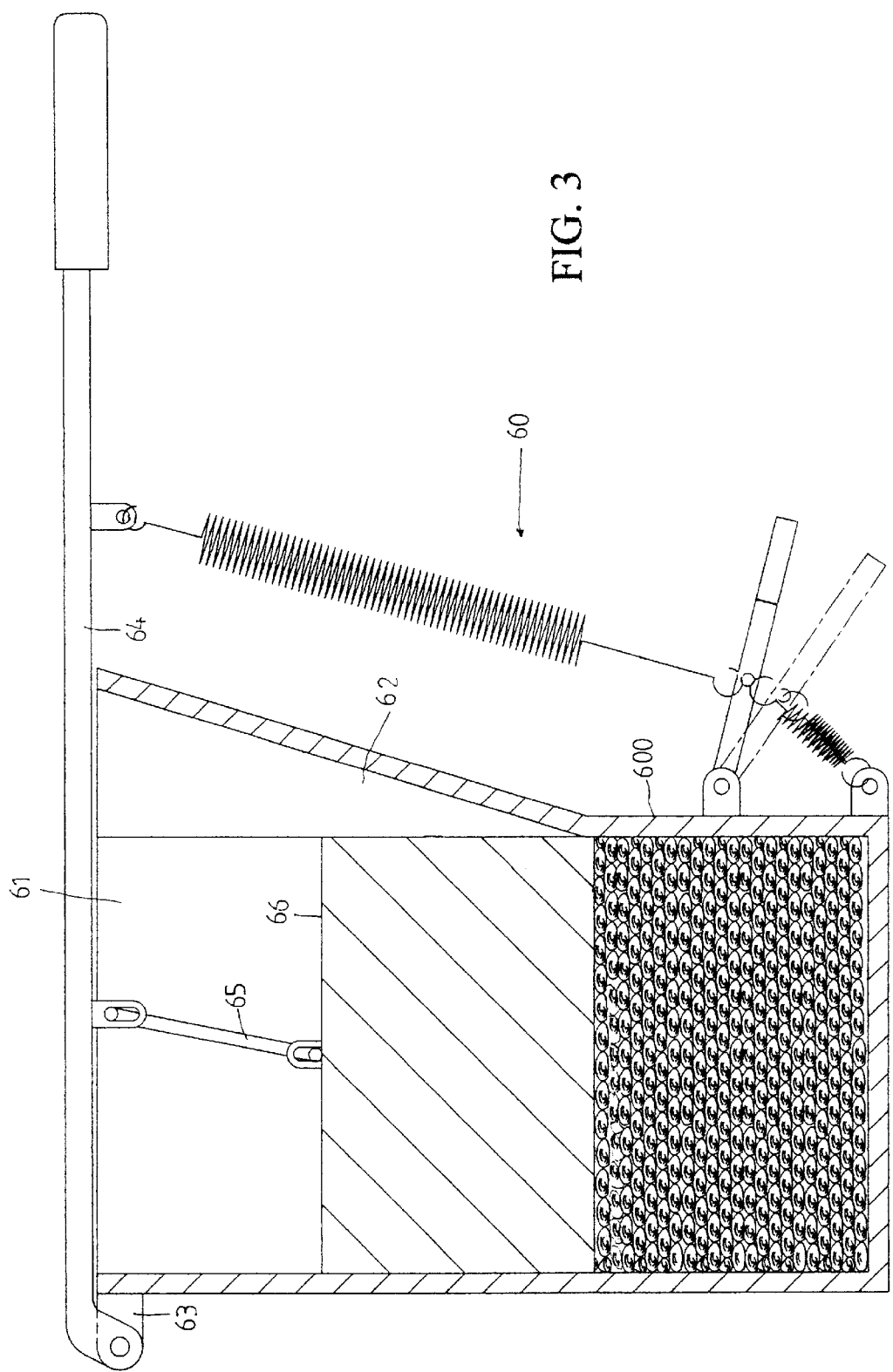
FIG. 3 is a sectional view of waste storage device of FIG. 1 where wastes are compressed.

Referring to FIG. 3, the waste storage device 60 comprises a third container 600, a receiving space 61 formed in third container 600, a top opening 62 on one side being downwardly tapered for guiding waste (e.g., cotton, bands or the like) to drop into receiving space 61, a hinge 63 on the top periphery of third container 600 opposite to opening 62, a spring-loaded lever 64 having one end coupled to the hinge 63, a connecting rod 65 having one end pivotably coupled to the bottom of lever 64, and a plunger 66 pivotably coupled to the other end of connecting rod 65 being sized to conform to the inner diameter of the lower part of third container 600 so as to be capable of sliding therein. In the invention, the frictional coefficient between plunger 66 and inner surface of third container 600 is substantially zero.

Figure 4:
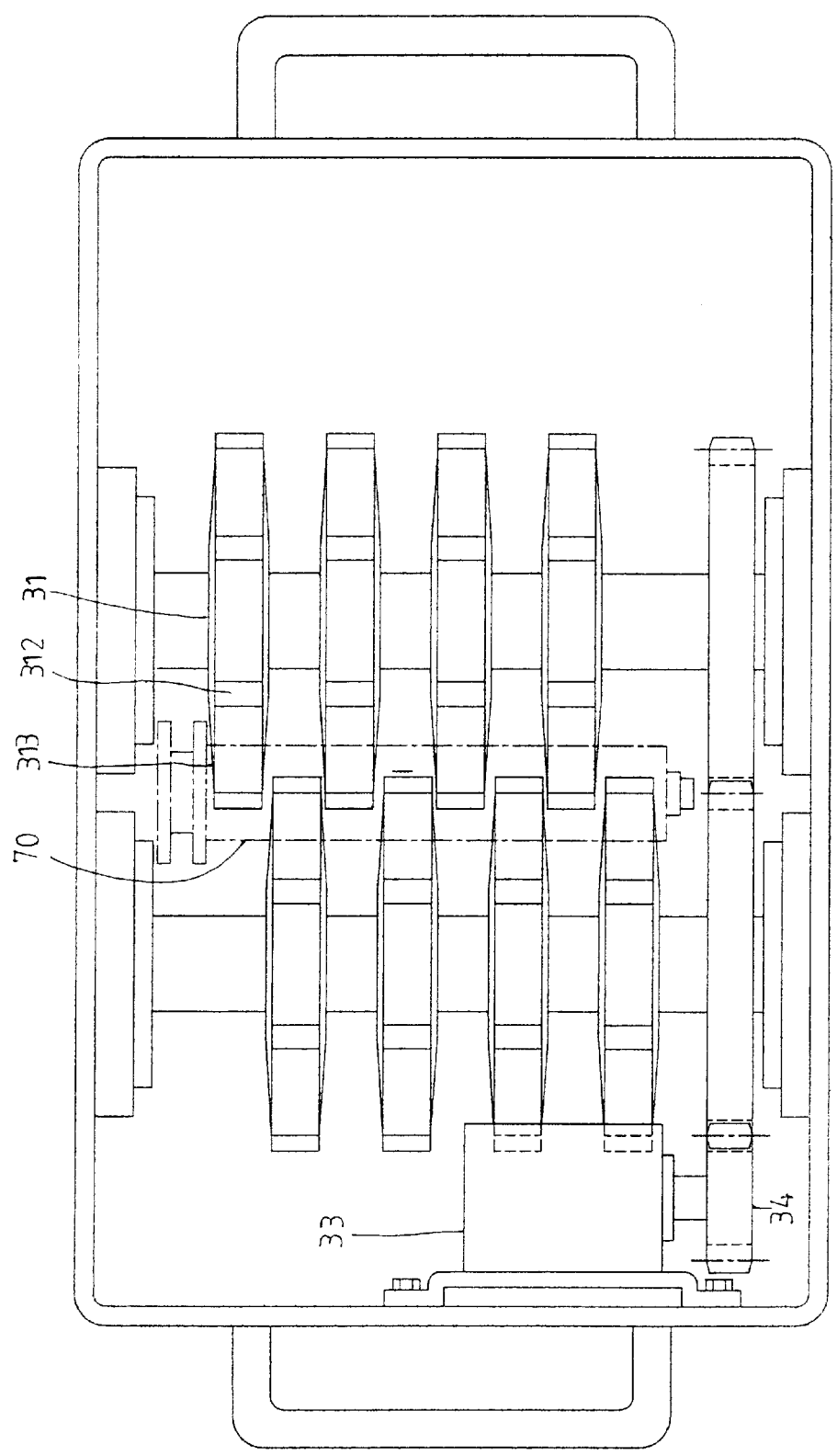
FIG. 4 is a top plan view of FIG. 1 apparatus where the top is schematically removed to show the interior features.
Figure 5:
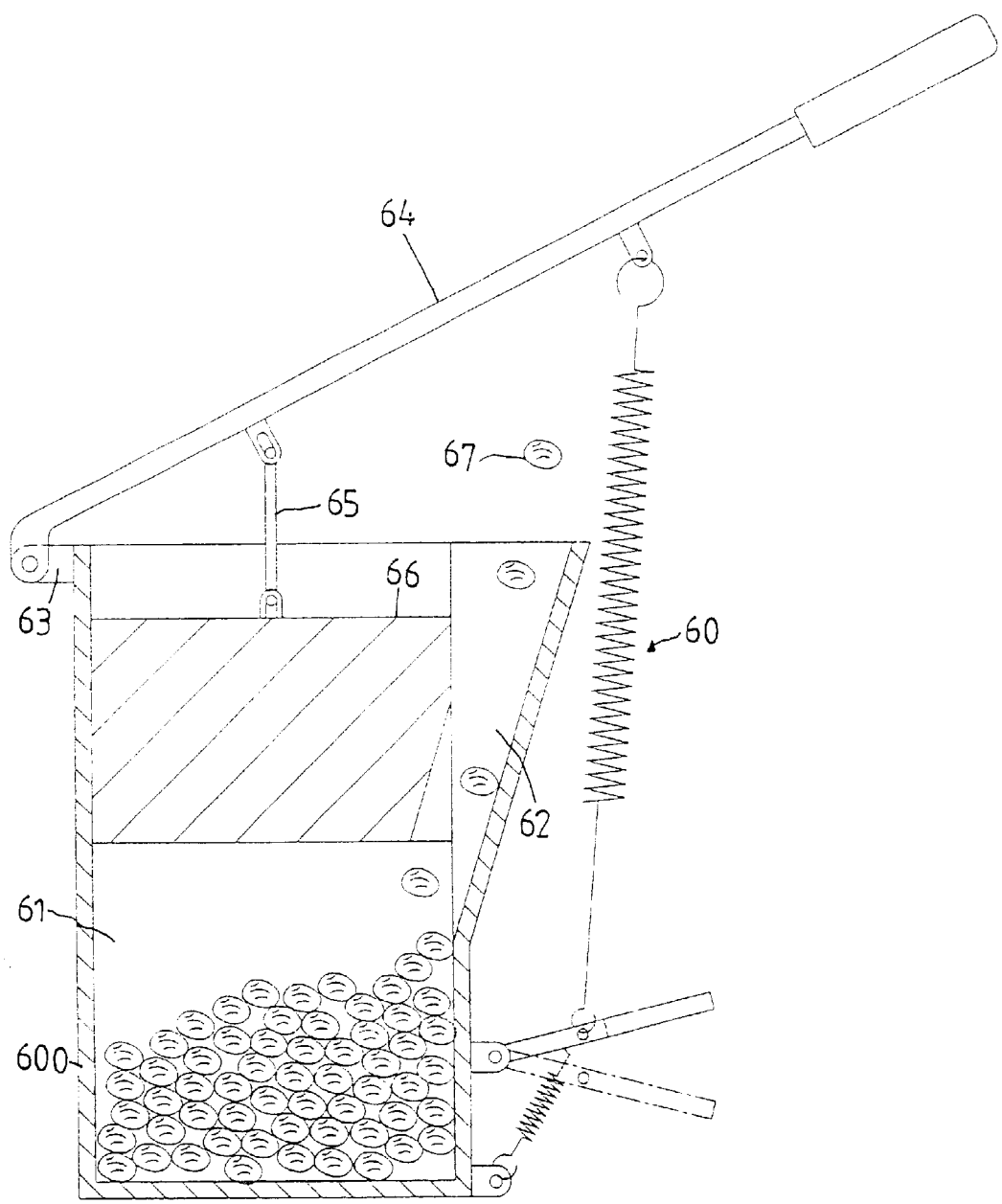
FIG. 5 is a view similar to FIG. 3 where wastes are falling into receiving space.

Referring to FIG. 2 again specifically, the hollow metal needle 71 of a first used syringe 70 is inserted into slit 11 while the piston syringe portion of the hypodermic syringe 70 is held on top of slit 11. Then insert a second used syringe 70 into slit 11, thus pushing the first used syringe 70 forward. In this manner, the hollow metal needle of used syringe 70 will be pulverized by the pulverizing device 21 once contacting while moving along slit 11. It is designed that a high temperature will be generated during the pulverizing process of the hollow metal needle of syringe 70, Hence, virus remained on hollow metal needle of syringe 70 will be substantially destroyed. Thus formed powder are then dropped into first container 24 through channel 23. Moreover, as the syringes 70 being pushed forward continuously the front syringe 70 will eventually move to hole 72 and drop into crushing device 30. Referring to FIGS. 4 and 5 in conjunction with FIGS. 1 to 3, the dropped piston syringe portion of syringe 70 will be pressed by the cams 312 of the sets of blade wheels 31 prior to cutting into pieces 50 by blades 313 of the sets of blade wheels 31. Thus formed pieces are then dropped into second container 35 (FIG. 2). As shown in FIGS. 3 and 5, user may lift lever 64 up to form a passageway in the bottom of opening 62 for permitting to throw waste (e.g., cotton, bands or the like) into waste storage device 60 to store in receiving space 61 through the opening 62 and the passageway. Once the waste is full user may push down lever 64 to cause plunger 66 to compress the waste in third container 600.

In brief, hollow metal needles and piston syringe portions of used syringes are crushed to powder and pieces respectively in body 11 while being pasteurized. Moreover, waste (e.g., cotton, bands or the like) is compressed in waste storage device 60 separately. In other words, the apparatus can effectively crush, pasteurize, and recycle used hypodermic syringes and compress waste generated in a hospital.

While the invention has been described by means of specific embodiments, numerous modifications and variations could be made thereto by those skilled in the art without departing from the scope and spirit of the invention set forth in the claims.

What is claimed is:

1. A recycling apparatus comprising a body; a slit on top of said body having a width only permitting a piston syringe portion of a hypodermic syringe to pass through while holding a hollow metal needle of said syringe thereon, said slit having a hole on one end for permitting said piston syringe portion of said syringe to drop into said body; a rear pasteurizing mechanism inside said body under said slit comprising a pulverizing device for pulverizing said needle of said syringe into powder, a first drive source for driving said pulverizing device, a channel extended downward from said first drive source for guiding said dropped powder, and a bottom first container; a front crushing mechanism inside said body under said hole comprising two sets of parallel blade wheels, a second drive source, a reduction gear for reducing a rotating speed of said second drive source, a loop member coupled between said reduction gear and one set of said blade wheels for transmitting a power of said second drive source to one set of said blade wheels, and a bottom second container; and a waste storage mechanism attached to the front side of said body and comprising a third container, a top downwardly tapered opening, a hinge on the top edge of said third container opposite to said opening, a spring-loaded lever having one end coupled to said hinge, a connecting rod having one end pivotably coupled to the bottom of said lever, and a plunger pivotably coupled to the other end of said connecting rod being capable of sliding in said third container; wherein in one state of use sequentially insert said needles of said used syringes into said slit with said piston syringe portion of said syringe held on said slit, push said used syringes forward to cause said needles of said syringes to contact said pulverizing device to be ground into powder while being pasteurized, said powder are dropped into said first container through said channel, said remained piston syringe portion of each of said syringes eventually drops into said crushing mechanism through said hole, said dropped piston syringe portion of each of said syringes is pressed and cut into pieces by said sets of said blade wheels, and said pieces are dropped into said second container; and in the other state of use lift said lever up to allow waste to store in said third container through said opening, and push down said lever to cause said plunger to compress said waste.

2. The apparatus of claim 1, wherein said pulverizing device is a grinding wheel.

3. The apparatus of claim 1, wherein said loop member is a belt.

* * * * *